United States Patent
Luo

(10) Patent No.: US 12,171,944 B1
(45) Date of Patent: Dec. 24, 2024

(54) PATIENT INTERFACE ASSEMBLY

(71) Applicant: DCSTAR INC, New York, NY (US)

(72) Inventor: David Luo, New York, NY (US)

(73) Assignee: DCSTAR INC., New York, NY (US)

(*) Notice: Subject to any disclaimer, the term of this patent is extended or adjusted under 35 U.S.C. 154(b) by 0 days.

(21) Appl. No.: 18/540,141

(22) Filed: Dec. 14, 2023

(51) Int. Cl.
*A61M 16/06* (2006.01)
*A61M 16/08* (2006.01)

(52) U.S. Cl.
CPC .... *A61M 16/0622* (2014.02); *A61M 16/0816* (2013.01); *A61M 2210/0618* (2013.01); *A61M 2210/0625* (2013.01)

(58) Field of Classification Search
CPC ............. A44B 11/266; A44D 2203/00; A61M 16/0057; A61M 16/0066; A61M 16/0069; A61M 16/024; A61M 16/06; A61M 16/0605; A61M 16/0611; A61M 16/0616; A61M 16/0622; A61M 16/0633; A61M 16/0638; A61M 16/0666; A61M 16/0683; A61M 16/0694; A61M 16/08; A61M 16/0816; A61M 16/0825; A61M 16/0866; A61M 16/0875; A61M 16/10; A61M 16/1075; A61M 16/109; A61M 16/16; A61M 16/20; A61M 16/208; A61M 16/22; A61M 2016/0027; A61M 2016/0661; A61M 2202/0085; A61M 2202/0225; A61M 2205/3368; A61M 2205/42; A61M 2206/14; A61M 2207/00; A61M 2210/0618; A61M 39/10; A62B 18/084; A62B 9/04; F16L 27/04; H01F 7/0263; Y10T 24/1959; Y10T 24/32
See application file for complete search history.

(56) References Cited

U.S. PATENT DOCUMENTS

| | | | |
|---|---|---|---|
| 6,581,594 B1* | 6/2003 | Drew | A61M 16/0633 128/207.12 |
| 2003/0196656 A1* | 10/2003 | Moore | A61M 16/0622 128/201.22 |
| 2013/0213401 A1* | 8/2013 | Haibach | A61M 16/0633 128/205.25 |
| 2014/0150798 A1* | 6/2014 | Fong | A61M 16/0825 128/206.21 |

* cited by examiner

*Primary Examiner* — Annette Dixon
(74) *Attorney, Agent, or Firm* — Birch, Stewart, Kolasch & Birch, LLP

(57) ABSTRACT

A patient interface assembly with optimized connection methods and improved air-tightness. The patient interface assembly forms a complete channel to deliver positive pressure air when connected with an air supply tube and a ventilator. The patient interface assembly includes a patient interface pad, a frame, an elbow assembly, and a quick-release connector. The patient interface pad is fixedly connected to one end of the elbow assembly. The frame is positioned between the elbow assembly and the patient interface pad. The other end of the elbow assembly is connected to the quick-release connector. By reducing the connection steps between parts, the air-tightness of the patient interface assembly is enhanced, and the patient interface assembly is adaptable to various types of frames.

18 Claims, 19 Drawing Sheets

PATIENT INTERFACE ASSEMBLY

TECHNICAL FIELD

The disclosure provides a patient interface assembly that pertains to the field of respiratory therapy technology, especially sleep breathing disorders such as Obstructive Sleep Apnea (OSA), involving aspects such as inter-component connection, positioning, and modular matching.

BACKGROUND

Obstructive Sleep Apnea (OSA) is a potentially severe sleep disorder characterized by repeated collapse of the upper airway during sleep, leading to obstructive apneas, hypoventilation, or breath effort-related micro-arousals. OSA is the most common sleep-related breathing disorder. The condition is most commonly found in older males, but it can also happen to females and children. This type of sleep apnea occurs when the muscles at the back of the throat relax, which support the soft palate, the triangular tissue hanging from the soft palate (uvula), the tonsils, the side walls of the throat, and the tongue. If these muscles relax, the airway narrows or closes as one breathes in, and patients cannot take adequate air and the oxygen level in the blood drop. The brain senses the impossibility of breathing and can only briefly rouse the patient to reopen the airway. This pattern repeats itself 5 to 30 times or more each hour, preventing the patient from reaching a restful deep sleep stage. Further, some adverse complications may arise, such as cognitive dysfunction, cardiovascular complications, pulmonary hypertension or right heart failure, and gastroesophageal reflux disease. Due to the complexity of OSA's etiology and the individual variations in the anatomical characteristics of the upper airway, the severity of the condition varies among patients. Coupled with the uncertain efficacy of different treatment methods, this leads to a variety of treatment options for OSA. As a result, personalized treatment has become the developing trend in OSA therapy. CPAP (Continuous Positive Airway Pressure) is the primary treatment method for adult OSA patients. At night, patients wear a CPAP interface pad over their nose and mouth, which is connected to a ventilator through a tube. This ventilator pumps pressurized air into the airway, keeping it open during sleep. Even though this method of air delivery is effective, there are still issues with the treatment in terms of comfort, ease of use, and compliance, leading to as many as 83% of patients not adhering to the ventilator treatment's method.

When patients are choosing assemblies for sleep apnea treatment, they face considerations in various aspects, involving the following areas: 1. The comfort of the patient interface assemblies: The shape, contour, and size of each component in the patient interface assembly should fit the facial contour or conform to the facial curves. Through reasonable design and material selection, it ensures that the patient interface assemblies can fit the face, making the assembly overall lighter, reducing the feeling of a foreign object, and making it more practical and aesthetically pleasing. 2. The air-tightness of the respiratory machine system: Apart from the exhaust port and the anti-asphyxiation valve, there are at least five leakage risks in the respiratory machine system: between the face and the patient interface pad, between the patient interface pad and the frame, between the frame and the elbow, between the elbow and the air supply hose, and between the air supply hose and the machine. Improving or simplifying the connection methods between components can make the connections between components more solid and effectively prevent gas leakage, enhancing the therapeutic effect. 3. Diversity of the Frame: Factors such as the weight of the frame, the length of the extending arms, and their number, etc. can have different forms. The frame can adopt various shapes and sizes to accommodate different facial features and personal preferences of patients.

The majority of mask or nasal mask systems on the current market exhibit the following disadvantages: 1. By designing the structure at each interface and improving the application of sealing materials, the goal of reducing the risk of air leakage in system components can be achieved. However, the commonly used sealing material, silicone, may be affected by aging during its use. This can lead to changes in its performance and appearance, subsequently diminishing its air-tightness. 2. In the system assembly, the frame plays important roles in support, positioning, and connecting. However, patients have different preferences, and their requirements for its shape and size vary. In existing system components, the relationship between the frame and the mask, and relationship between the frame and the elbow are one-to-one matching relationships. Only by connecting the mask, frame, and elbow in a one-to-one manner can a complete component be achieved. As a result, most patients, while considering the comfort of the mask, are unable to choose their preferred frame style, which reduces their satisfaction with the system components.

Therefore, the disclosure improves the way each part of the patient interface assembly connects, enhancing the air-tightness of the assembly and realizing more frame's matching that patients need. This makes the entire patient interface assembly more user-friendly, easier to assemble, seal, clean, and maintain, thereby improving product performance.

SUMMARY

Based on this, it is necessary to address the aforementioned shortcomings and provide a patient interface assembly that is easy to assemble and has good sealing properties.

In one embodiment, a patient interface assembly is provided. The patient interface assembly is configured to longitudinally contact an area between a nose bridge and a chin to form a seal to an oral airway and a nasal airway, or longitudinally contact an area between the nose bridge and an upper lip to form a seal to a nasal airway. Additionally, the patient interface assembly is also configured to communicate equipment with the airways to transmit positive pressure air or breathable gas for medical treatment. The patient interface assembly includes: a patient interface pad, which consists of a front interface end, a rear interface end, a support element that at least partially contacts a side wall of a frame, a sealing element with a cushioning structure, and a positioning component that contacts the frame. The front interface end of the patient interface pad is designed to connect to an elbow assembly. The rear interface end is configured to seal at least one airway: the elbow assembly includes an elbow with a first interface end, a second interface end, and a shaft bending annular channel. The elbow includes a fixed structure configured to connect with the front interface end of the patient interface pad, and additionally, a baffle is set up on the elbow assembly to limit the forward and backward movement of the frame: the frame includes a positioning section, at least one through-opening, and support plates extending around from the through-opening. The positioning section is configured to position the frame onto the patient interface pad; and an exhaust port is located on the patient interface pad, allowing exhaled waste gas to flow from the inside of the patient interface pad to an external environment. The positioning component has a contour shape that matches the positioning section on the frame, configured to limit a relative rotation between the frame and the patient interface pad.

In one embodiment, the patient interface pad is a nasal mask or a face mask, and the rear interface of the patient interface pad seals at least a nasal airway.

In one embodiment, the cushioning structure of the sealing element is accordion-shaped or an air cushion.

In one embodiment, a shape of baffle on the elbow assembly includes, but is not limited to, options such as circular, triangular, and square.

In another embodiment, a patient interface assembly is provided. The patient interface assembly is configured to longitudinally contact an area between a nose bridge and a chin and form a seal to an oral airway and a nasal airway, or longitudinally contact an area between the nose bridge and an upper lip, and form a seal to a nasal airway, and the patient interface assembly is also configured to communicate equipment with the airways to transmit positive pressure air or breathable gas for medical treatment. And the patient interface assembly includes: a patient interface pad, which consists of a front interface end, a rear interface end, a support element that at least partially contacts a side wall of a frame, a sealing element with a cushioning structure, and a positioning component that contacts the frame. The front interface end of the patient interface pad is designed to connect to an elbow assembly. The rear interface end is configured to seal at least one airway. The elbow assembly includes a connector with a first end portion and a second end portion, and an elbow with a first interface end, a second interface end, and a shaft bending annular channel. The first end portion of the connector includes a fixed structure configured to connect with the front interface end of the patient interface pad. The second end portion is designed to connect with the first interface end of the elbow. A baffle is set up on the elbow assembly to limit the forward and backward movement of the frame: the frame includes a positioning section, at least one through-opening, and support plates extending around from the through-opening. The positioning section is configured to position the frame onto the patient interface pad; and an exhaust port is located on the elbow assembly, allowing exhaled waste gas to be discharged from the elbow assembly to the external environment. The positioning component has a contour shape that matches the positioning section on the frame, configured to limit a relative rotation between the frame and the patient interface pad.

In one embodiment, a fixed structure of the connector in the elbow assembly includes one or more of a hinge, a ball socket, a snap-fitting, or a magnet, which is connectable to the front interface end of the patient interface pad.

In one embodiment, a connection method between the connector and the elbow includes one or more of a hinge, a ball socket, a snap-fitting, or a magnet.

In one embodiment, an overall height range of the elbow assembly is at or between 30 to 80 mm.

In another embodiment, a patient interface assembly is provided. The patient interface assembly is configured to longitudinally contact an area between a nose bridge and a chin and form a seal to an oral airway and a nasal airway, or longitudinally contact an area between the nose bridge and an upper lip, and form a seal to a nasal airway, and the patient interface assembly is also configured to communicate equipment with the airways to transmit positive pressure air or breathable gas for medical treatment. The patient interface assembly includes: a patient interface pad, which consists of a front interface end, a rear interface end, a support element that at least partially contacts a side wall of a frame, a sealing element with a cushioning structure, and a positioning component that contacts the frame. The front interface end of the patient interface pad is designed to connect to a first interface end of an elbow assembly. The rear interface end is configured to seal at least one airway. The elbow assembly includes a connector with a first interface end and a second interface end, and an elbow with a first interface end, a second interface end, and a shaft bending annular channel. The elbow includes a fixed structure configured to connect with the front interface end of the patient interface pad, the second interface end is configured to rotatably connect to a quick-release connector. Additionally, a baffle is set up on the elbow assembly to limit the forward and backward movement of the frame: the frame includes a positioning section, at least one through-opening, and a support plate extending around from the through-opening. The positioning section has a contour shape that conforms to a portion of the frame, configured to position the frame onto the patient interface pad; and the positioning component has a shape that conforms to a portion of the contour of the frame, and is configured to limit a relative rotation between the frame and the patient interface pad; and the quick-release connector includes an upper end, a lower end, and a fixing component, and the upper end is configured to be directly and detachably connected to the second interface end of the elbow assembly; and an exhaust port is located on the elbow assembly, allowing exhaled waste gas to be discharged from the elbow assembly to external environment. Without the influence of external forces, a connection force between the patient interface pad and the elbow assembly is greater than the force required to separate them.

In one embodiment, the fixed structure on the elbow assembly includes one or more of a hinge, a ball socket, a snap-fitting, or a magnet.

In one embodiment, a form of the positioning component can be a protrusion, groove, magnet, or contour, and its shape can be circular, triangular, square, or any other shape.

In one embodiment, a positioning section on the frame can be circular, triangular, and square or other shape that matches the positioning component.

In another embodiment, a patient interface assembly is provided. The patient interface assembly is configured to longitudinally contact an area between a nose bridge and a chin and form a seal to an oral airway and a nasal airway, or longitudinally contact an area between the nose bridge and an upper lip, and form a seal to a nasal airway, and the patient interface assembly is also configured to communicate equipment with the airways to transmit positive pressure air or breathable gas for medical treatment. The patient interface assembly includes: a patient interface pad, which consists of a front interface end, a rear interface end, a support element that at least partially contacts a side wall of a frame, a sealing element with a cushioning structure, and a positioning component that contacts the frame. The front interface end of the patient interface pad is designed to connect to a first interface end of an elbow assembly. The rear interface end is configured to seal at least one airway. The elbow assembly includes a connector with a first interface end and a second interface end, and an elbow with a first interface end, a second interface end, and a shaft bending annular channel. The elbow includes a fixed structure configured to connect with the front interface end of the patient interface pad, the second interface end is configured to rotatably connect to a quick-release connector. Additionally, a baffle is set up on the elbow assembly to limit the forward and backward movement of the frame: the frame includes a positioning section, at least one through-opening, and a support plate extending around from the through-opening. The positioning section has a contour shape that conforms to a portion of the frame, configured to position the frame onto the patient interface pad; and an exhaust port is located on the elbow assembly, allowing exhaled waste gas to flow from the inside of the elbow assembly to an external environment: the quick-release connector includes an upper end, a lower end, and a fixing component, and an upper end is configured to be directly and detachably connected to the second interface end of the elbow assembly. The positioning component has a contour shape that matches the positioning section on the frame, configured to limit a relative rotation between the frame and the patient interface pad.

In one embodiment, the support plate on the frame extends from a perimeter of the through-opening towards the side facing a face, forming any contour.

In one embodiment, a form of the exhaust port can be a through-hole or a mesh-like structure, and when the exhaust port is mesh-like, a material of the exhaust port is noise reduction material.

In one embodiment, the fixing component of the quick-release connector is located at the upper end of the quick-release connector. The fixing component is a clip, a snap-fit, or a magnet.

In another embodiment, a patient interface assembly is provided. The patient interface assembly is configured to longitudinally contact an area between a nose bridge and a chin and form a seal to an oral airway and a nasal airway, or longitudinally contact an area between the nose bridge and an upper lip, and form a seal to a nasal airway, and the patient interface assembly is also configured to communicate equipment with the airways to transmit positive pressure air or breathable gas for medical treatment. The patient interface assembly includes: a patient interface pad, which consists of a front interface end, a rear interface end, a support element that at least partially contacts a side wall of a frame, a sealing element with a cushioning structure, and a positioning component that contacts the frame. The front interface end of the patient interface pad is designed to connect to an elbow assembly. The rear interface end is configured to seal at least one airway. The front interface end of the patient interface pad has an outer opening, an inner opening, and an annular wall. A diameter of the outer opening is larger than a diameter of the inner opening; and the elbow assembly includes an elbow with a first interface end, a second interface end, and a shaft bending annular channel, and an anti-asphyxia valve structure with a silicone piece and an anti-asphyxia valve. The elbow includes a fixed structure configured to connect with the front interface end of the patient interface pad. The anti-asphyxia valve is configured as at least one set on the elbow: A baffle is set up on the elbow assembly to limit the forward and backward movement of the frame; the frame, including a positioning section, at least one through-opening, support plate extending around from the through-opening, where the positioning section is configured to position frame onto the patient interface pad; and the positioning component has a contour shape that matches the positioning part on the frame and is configured to limit a relative rotation between the frame and the patient interface pad; and an exhaust port is located on the elbow assembly, allowing exhaled waste gas to flow from the inside of the patient interface pad to an external environment. When not subjected to external forces, a connection force between the patient interface pad and the elbow assembly is greater than the force required to separate them.

In one embodiment, the anti-asphyxia valve is in a circular shape, an elliptical shape, a semicircular shape, or a triangular shape.

In one embodiment, the connection method between the support element of the patient interface pad and the sealing element is molding, adhesive bonding, or mechanical connection or a combination of the connection methods.

In one embodiment, a form of the exhaust port is a through-hole or a mesh-like structure, and when the exhaust port is hole-shaped, the exhaust port includes a configuration for use with an external connector which includes an external connection snap-fitting and noise reduction material.

Implementing the patient interface assembly in the disclosure provides at least the following beneficial effects:

1. Reducing the connection steps between components results in fewer failure points, reducing the overall product's malfunction rate and therefore enhancing the overall component's air-tightness. In the market, most mask systems or nasal systems are assembled through the connection method of patient interface pad-frame-elbow. This common approach includes two uncontrollable leakage risks, which are between the patient interface pad and the frame, and between the frame and the elbow. but complex and lengthy installation steps can increase the risk of operational errors, leading to incorrect or incomplete assembly. This can subsequently impact the product's performance and reliability, resulting in issues like poor sealing, improper fitting, and wear and tear. When patients are unfamiliar with the assembly process of the components, there's a high likelihood of situation of air leaks after assembly. Given that there are at least 4 to 5 fundamental connections within the entire treatment system, it makes it more challenging for patients to identify the reason of the leak. After prolonged use by the patient, since the patient interface assembly needs to be frequently disassembled and cleaned, the sealing at the connection area is highly susceptible to external damage, leading to reduced air-tightness. Directly connecting the patient interface pad to the elbow assembly and eliminating the step of connecting the patient interface pad to the frame has following advantages: a. When the gas is in the patient interface assembly, it only needs to pass directly through one channel, with fewer gaps when flowing through the channel, reducing the risk of leakage in the whole assembly: b. The assembly process is simplified. When patients assemble the components, they don't need to install them one by one. They only need to position the frame on the surface of the patient interface pad, and connect the elbow assembly to the patient interface pad. The patient interface pad and the elbow assembly automatically form a position to accommodate the frame, and can limit the relative movement between the frame and the two, making it easier for patients to assemble the new product. c. The installation steps are redesigned, reducing the connection points from two to one, letting the overall structure that is constructed by all the respiratory components simplified, reducing the chances of errors during the installation process and decreasing the occurrence of poor or incorrect assembly. By designing a user-friendly installation interface and providing clear guidance, and by using the assembly process that is easy to operate, it allows users to complete product assembly more effortlessly and reducing potential points of failure during installation, thereby lowering the failure rate during the product's operation.

2. Modular combination, more choices. Because the installation step of the frame is eliminated, the importance of the frame in the installation steps is diminished. The frame is limitingly positioned to some extent by the groove formed by the connection of the baffle of the elbow assembly with the patient interface pad. Therefore, the basic part of the frame only needs to include the sidewall that can accommodate part of the mask, the through-opening that allows the elbow assemblies to pass through and matches with the patient interface pad, and the positioning section on the frame that can be matched with the mask positioning component. Apart from the basic parts, the frame can have more choices on its shape design, which can provide corresponding frames for patients who have different needs or preferences. There's no longer a need to design frames with different connection methods for different elbow and patient interface pad. It's not necessary to consider the impact of frame on the overall air-tightness of the whole assembly, and the focus can solely be on the comfort of the patient when wearing it. In production, the basic connection structure between the patient interface pad and the elbow assembly is also simplified, while important functional structures such as exhaust holes and anti-asphyxiation valves do not need to be changed. The reduction in the processing steps for the overall connection structure means that, with the connection between the elbow assemblies and the patient interface pad being fixed, it's only necessary to modularly develop a structurely simple frame. This greatly reduces the processing complexity and R&D costs of the patient interface assembly, while offering a variety of frame combinations to meet various user's needs.

3. The connection between the components is more stable. Compared to the connection of the patient interface pad-frame-elbow; the connection method of the patient interface pad-elbow assembly is more stable. The direct connection design of the elbow assemblies and the patient interface pad, based on the original connection method, adds radial support from the elbow assembly to the frame and restricts and secures the frame through the baffle of the elbow assembly. The connection points have also been simplified from two to one, making it less likely to come loose. Without the application of external force, in the connection method of the patient interface pad-frame-elbow; the patient interface pad is subjected to the gravitational pull of the frame and the elbow: while, in the connection method of the patient interface pad-elbow assembly, the patient interface pad is only subjected to the gravitational pull of the elbow assembly. Comparing the two, the assembly method of the former increases the risk of the patient interface assembly falling off under the influence of tension. In contrast, the assembly design of the latter reduces the risk of component detachment, making it more stable and less prone to falling off.

4. Compared to other products with quick-release elbows, the patient interface assembly has fewer components and is lighter in overall weight. Most existing products connect the elbow assembly, which has a clip structure on both sides, directly to the frame, and the lower end of the elbow is detachably connected to the air supply hose. At this time, due to the presence of the quick-release connection structure on the elbow assembly, it adds weight to the patient interface system. Therefore, by separating the quick-release system on the elbow assembly and designing the elbow assembly to be directly detachable with the patient interface pad, the overall weight of the patient interface assembly is reduced. Meanwhile, quick-release parts can be selected based on the personal wearing preferences. When the patient interface assembly is directly connected through the elbow; the overall parts of the component are more lightweight and easier to use compared to the existing mask systems. By simplifying the structure of the elbow to reduce its weight and reducing the number of parts on the elbow; the overall number of components is reduced.

5. The simplification of individual component structures can reduce costs, and they are also easier to clean and more environmentally friendly: a. The design of the frame eliminates the snap-fitting connection structure, making the model structure simpler. This can reduce the processing steps and complexity, thereby lowering the costs during the processing and manufacturing process. Changes in corresponding mold making and corresponding mold-opening methods reduce the investment and maintenance costs of equipment and molds: simple component structures make it easier to conduct quality inspection and control, reducing the occurrence of defective products and lowering inspection costs. The simplified structure leads to a smaller volume and lighter weight, making stacking and placing components easier, thus reducing transportation costs. When the frame component is damaged, only a new frame needs to be replaced, and there are more choices available. There's no need to consider the connection issues between components, providing patients with a more comfortable experience. The assembly of modular components, for production, can extend the lifespan of each component, helping reduce energy consumption and waste material during the manufacturing process. By reducing energy consumption and waste material and recycling some components, carbon emissions in production are decreased, and the environment is protected. b. With the simplified design of frame and the corresponding adjustments of the patient interface pad and elbow assembly, it makes the product easier to use, there are fewer connections and fixtures in the components. As a result, they are easier to disassemble and clean when needed. The simple structure reduces the presence of hygiene blind spots and a concave-convex surface, minimizing the chances of impurities and dirt accumulation, making the cleaning process easier and more thorough. Complex components might require more detergents and tools for thorough cleaning, while simpler components achieve the same cleanliness with fewer quantities, reducing the use of chemical cleaning agents. This saves energy and time and is environmentally beneficial.

DETAILED DESCRIPTION

To make the objectives, features, and advantages of this disclosure more clear and understandable, the specific embodiments of this disclosure are described in detail below with reference to the accompanying drawings. In the following description, a lot of specific details are elaborated to facilitate a full understanding of this disclosure. However, this disclosure can be implemented in many ways other than those described here, and those skilled in the art can make similar improvements without departing from the essence of this disclosure. Therefore, the disclosure is not limited to the specific embodiments disclosed below.

Figure 9:
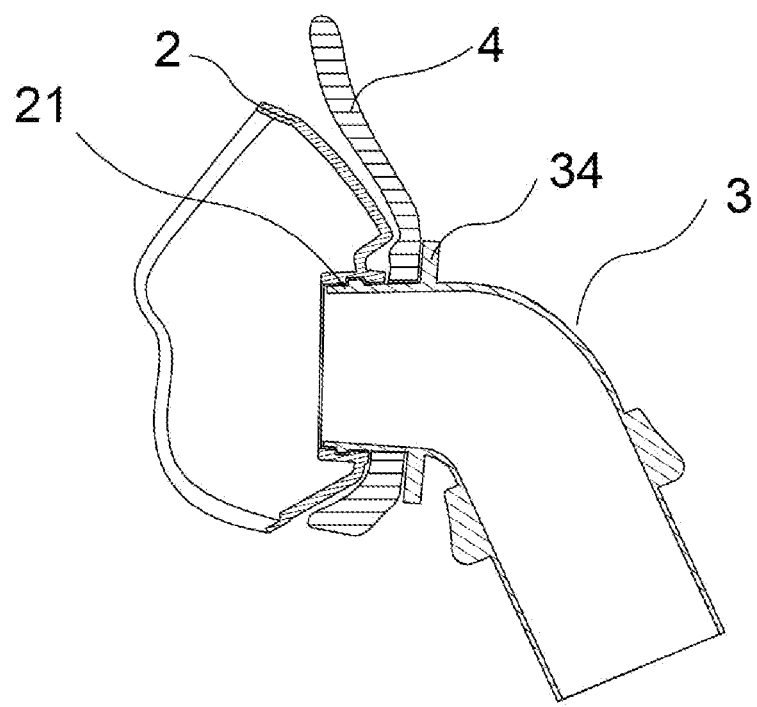
FIG. 9 shows a sectional view of the gap formed by the connection of a baffle of an elbow assembly and an patient interface pad in accordance with an embodiment.

The disclosure addresses the issue of inconvenient component connections in the existing face mask systems, providing a patient interface assembly 1 that simplifies the installation steps. This component includes a patient interface pad 2, a frame 4, an elbow assembly 3, and a quick-release connector 6. The patient interface pad 2 is connected and fixed to one end of the elbow assembly 3, as shown in FIG. 9, and the frame 4 is positioned between the elbow assembly 3 and the patient interface pad 2. The positioning component 25 on the patient interface pad 2 limits the left and right rotation of the framework 4, and the baffle 34 on the elbow assembly 3, in conjunction with the patient interface pad 2, limits the forward and backward movement of the frame 4. The other end of the elbow assembly 3 is connected to the quick-release connector 6, and the whole assembly forms a complete channel for delivering positive pressure air with the air supply tube and respirator. By reducing the connection steps between components, the air-tightness of the patient interface assembly 1 is improved, and it is adaptable to various frame 4, enhancing the satisfaction with using the frame 4 assembly.

Figure 13A:
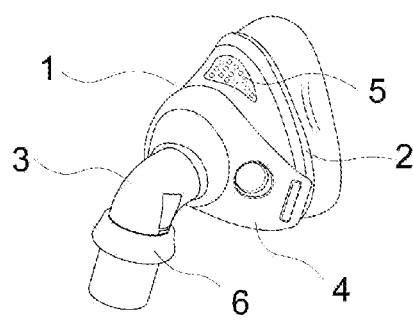
FIG. 13A and FIG. 13B show schematic diagrams of a patient interface assembly matching different types of patient interface pads in accordance with an embodiment.
Figure 13B:
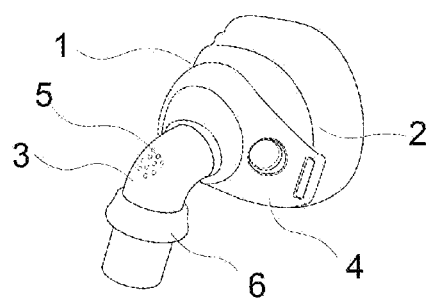

Moreover, specifically as shown in FIG. 13, in this embodiment, the patient interface assembly 1 is configured to longitudinally contact an area between a nose bridge and a chin and form a seal to an oral aiway and a nasal airway, or longitudinally contact the area between the nose bridge and upper lip and form a seal to a nasal airway, and the patient interface assembly 1 is also configured to communicate equipment with the airways to transmit positive pressure air or breathable gas for medical treatment.

Figures 17A, 17B, 17C:
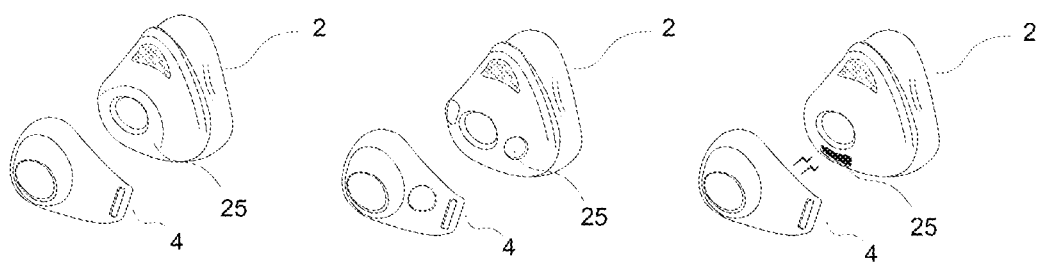
FIG. 17A, FIG. 17B, and FIG. 17C show schematic diagrams of the positioning method of a frame and a face mask in accordance with an embodiment.

Specifically, as shown in FIGS. 1-4, in the embodiment, the patient interface assembly includes a patient interface pad 2, an elbow assembly 3, a frame 4, a positioning component 25, and an exhaust port 5. The patient interface pad 2 comprises a front interface end 21, a rear interface end 22, a support element that at least partially conforms to the side contour of the frame 4, a sealing element 24 with a cushioning structure 241, and a positioning component 5 that contacts the frame 4. The front interface end 21 of the patient interface pad 2 is configured to connect with either the first interface end 311 of the elbow 31 in the elbow assembly 3 or connect with the first end portion 321 of the connector 32 in the elbow assembly 3. The rear interface end 22 is configured to seal at least one airway of the patient. The front interface end 21 includes an outer opening 211, an inner opening 212, and an annular wall 213. The diameter of the outer opening 211 is larger than that of the inner opening 212. The diameter of the outer opening 211 is approximately at or between 10 to 45 mm. The length of the annular wall 213 is at or between 1 to 15 mm, its thickness is approximately at or between 0.5 to 5 mm, and the fixed part's length between the patient interface pad 2 and the elbow assembly 3 is approximately at or between 1 to 15 mm. The diameter size range of the front interface end 21 ensures that positive pressure air can be smoothly delivered to the airway without the gas being dispersed due to the opening being too large, leading to a drop in air pressure and the treatment not achieving the expected results. The dimensions of the annular wall 213 ensure that the patient interface pad 2 and the elbow assembly 3 have a sufficient fixation area. The connection methods between the front interface end 21 and the elbow assembly 3 include but are not limited to snap-fitting, clips, magnetic attraction, hinges, ball sockets, etc., either singularly or in two or more methods. After being connected, the patient interface pad 2 the elbow assembly 3 can rotate relatively. The front interface end 21 is at least partially rigid and allows for slight deformation. The materials include, but are not limited to, polyethylene, polypropylene, polyester, silicone, polycarbonate, thermoplastic elastomers, either in one or more kinds of material. The material of the support element 23 includes, but is not limited to, polycarbonate, polyethylene, polypropylene, polyester, and the like. The sealing element 24 has a cushioning structure 241. The cushioning structure 241 can be on a part of the sealing element 24 or can encircle or cover a round of the sealing element 24. Its forms include, but are not limited to, accordion-like structures, air cushions, etc. The materials include, but are not limited to, silicone, thermoplastic elastomers, nylon, cotton, natural fabrics, either in one or more kinds of material. The support element 23 and the sealing element 24 are in a connected state when used. The connection methods include, but are not limited to, molding, adhesive bonding, mechanical connection, either in one or more of these methods. Furthermore, as shown in FIG. 17, at least one positioning component 25 is set on the patient interface pad 2. The positioning component 25 includes a contour shape that matches the positioning section 42 on the frame 4, a contour shape that conforms to the inner surface of a part of the frame 4, or magnetic attraction. In one embodiment, the height of the positioning component 25 is approximately at or between 0.1 to 8 mm. In another embodiment, the positioning component 25 is in the contour shape of the part of the support element 23 of the patient interface pad 2 that can be positioned, used to fit the contour of a part of the frame 4 to prevent relative rotation. The frame 4 is easily and quickly positioned on the outer surface of the patient interface pad 2 through the positioning component 25, preventing relative left and right displacement between the two. The positioning component 25 includes but is not limited to protrusions and grooves, and its contour shape includes but is not limited to random regular shapes such as circles, triangles, and squares. The positioning component 25 can be in full contact with the frame 4 or only in partial contact. The material of the positioning component 25 includes but is not limited to polyethylene, polypropylene, polycarbonate, polyester, silicone, thermoplastic elastomer, magnets, either in one or more kinds of material.

Figure 1:
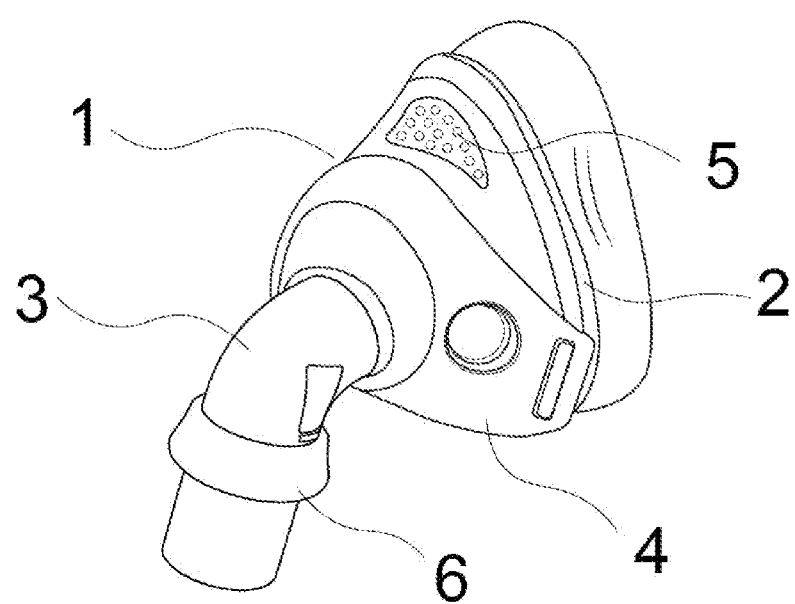
FIG. 1 shows a schematic diagram of the structure of a patient interface assembly in accordance with an embodiment.
Figure 2:
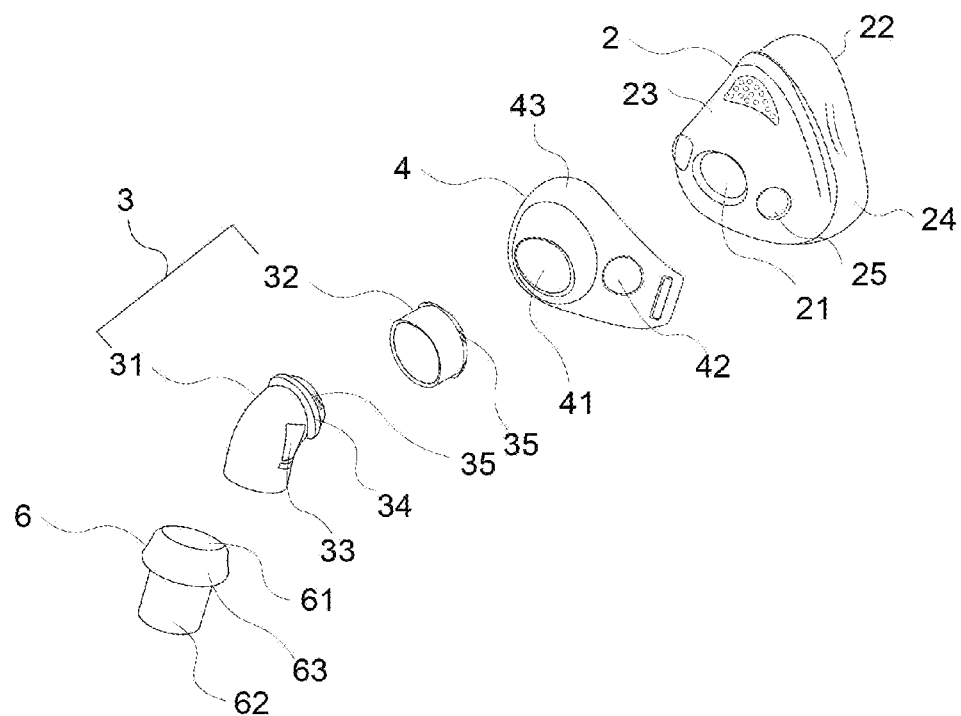
FIG. 2 shows an exploded schematic diagram of the structure of a patient interface assembly in accordance with an embodiment.
Figure 3:
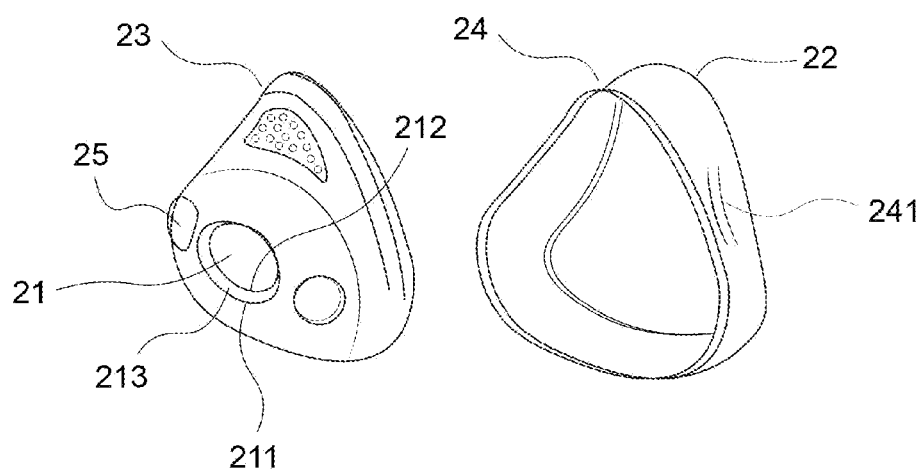
FIG. 3 shows an exploded schematic diagram of a patient interface pad in accordance with an embodiment.
Figure 4:
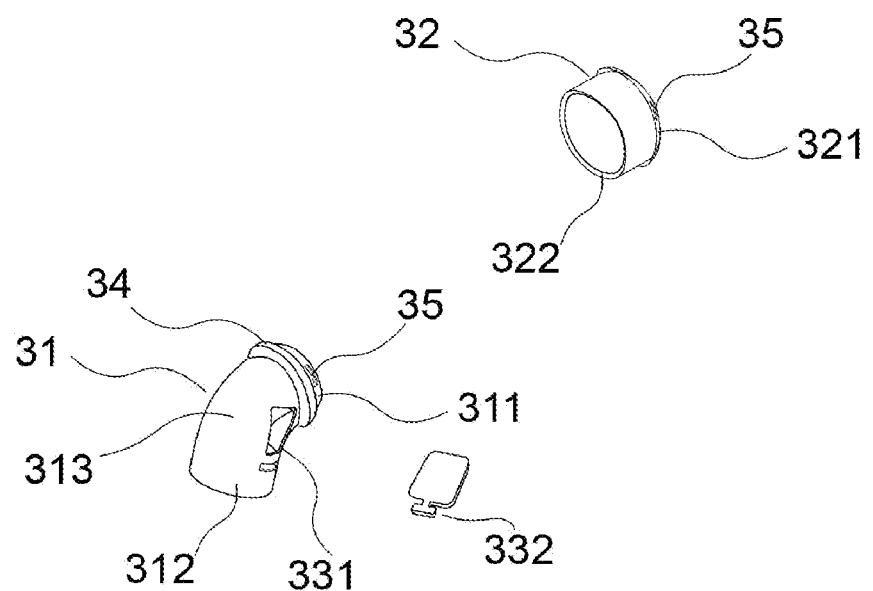
FIG. 4 shows an exploded schematic diagram of an elbow assembly in accordance with an embodiment.
Figure 18:
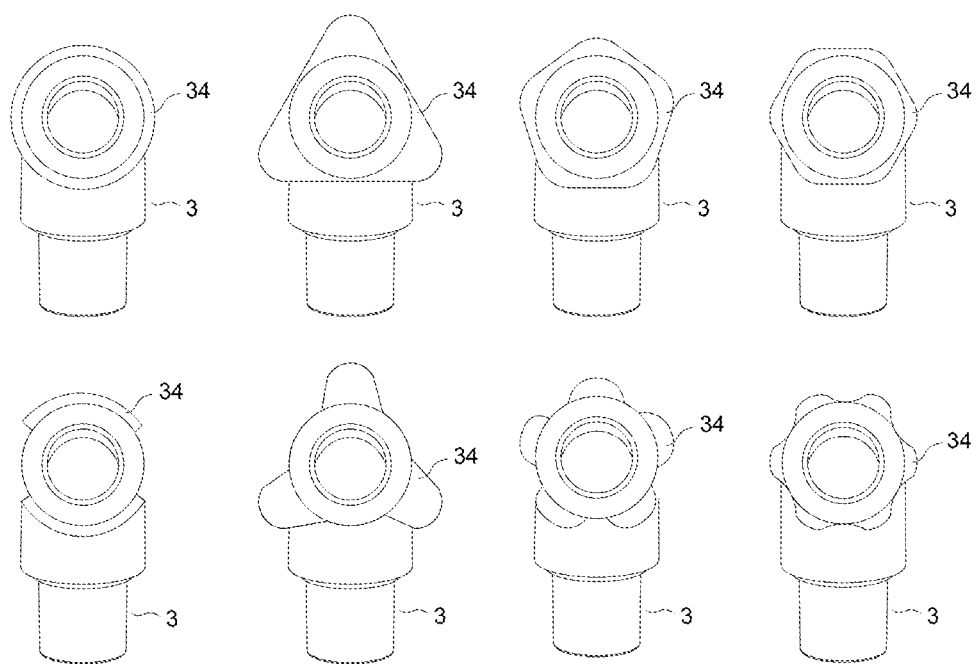
FIG. 18 shows a contour shape diagram of a baffle in accordance with Embodiment 1.
Figure 19A:
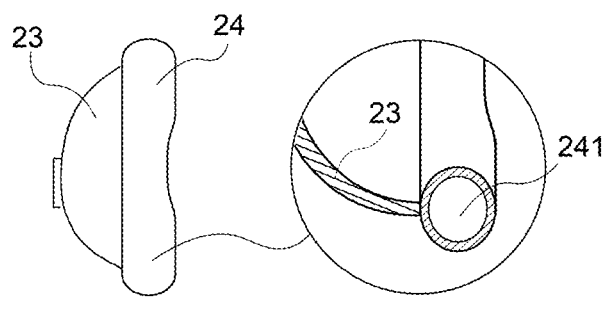
FIG. 19A and FIG. 19B show schematic diagrams of a cushioning structure of a sealing element in accordance with an embodiment.
Figure 19B:
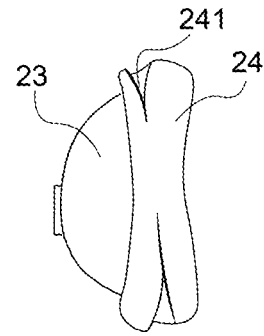

The elbow assembly 3 includes a connector 32 with a first end portion 321 and a second end portion 322. It also includes an elbow 31 with a first interface end 311, a second interface end 312, and an annular channel 313 that has a shaft bending (a shaft bending refers to a continuous force along the radial direction causing the shaft to bend, where "radial" refers to the direction along a diameter or radius, or perpendicular to the shaft direction). Additionally, the elbow assembly 3 includes an anti-asphyxia valve structure 33 with a silicone piece 332 and an anti-asphyxia valve 331, as well as a baffle 34. Furthermore, as shown in FIGS. 4 and 15, the elbow assembly 3 has two forms: 1. When the patient uses the connector 32, the first end portion 321 of the connector 32, through a fixed structure 35, is configured to directly connect with the front interface end 21 of the patient interface pad 2. The connection methods include but are not limited to a snap-fitting, a hinge, a ball socket, etc., in one method or more. The connector 32 and the patient interface pad 2 can rotate relative to each other. The second end portion 322 of the connector 32 is designed to connect with the first interface end 311 of the elbow 31. The connection methods include but are not limited to snap-fit, clip, hinge, ball socket, etc., in one method or more, and the second end portion 322 and the first interface end 311 can rotate relative to each other. The second interface end 312 of the elbow 31 is configured to connect with the quick-release connector 6 or the air supply tube. 2. When the patient only uses the elbow 31, the first interface of the elbow 31 is configured through the fixed structure 35 to directly connect with the front interface end 21 of the patient interface pad 2. The connection methods include but are not limited to snap-fit, hinge, ball socket, etc., and the elbow 31 and the patient interface pad 2 can rotate relative to each other. At least one anti-asphyxia valve structure 33 is set on the elbow 31. The anti-asphyxia valve 331 is configured to allow external gas to flow into the patient interface assembly 1. The silicone piece 332 is designed to prevent external gas from entering the component through the anti-asphyxia valve 331 when the CPAP machine is connected. The materials for the elbow assembly 3 include but are not limited to polyethylene, polyamide, polypropylene, polycarbonate, polyester, silicone, thermoplastic elastomer, in one of the materials or more. The overall height range of the connector 32 is at or between 10 to 30 mm, and the overall height range of the elbow 31 is at or between 30 to 80 mm, with both having a wall thickness at or between 0.5 to 5 mm. The outer diameter of the first end portion 321 of the connector 32 is approximately at or between 10 to 50 mm, and the outer diameter of the second end portion 322 is approximately at or between 10 to 50 mm. The outer diameter of the first interface end 311 of the elbow 31 is approximately at or between 1 to 15 mm, the outer diameter of the second interface end 312 is approximately at or between 1 to 15 mm, and the length of annular channel 313 is at or between 10 to 100 mm: The length of the first interface end 311 of the elbow 31 is approximately at or between 1 to 15 mm, and the length of the second interface end 312 of the elbow 31 is approximately at or between 1 to 15 mm. The anti-asphyxia valve 331 can be of any shape such as circular, elliptical, semicircular, triangular, etc., with an area range at or between 25 to 256 $mm^2$, ensuring that patients can still breathe normally when the machine is powered off. The length and thickness range of the elbow assembly 3 ensure that the various parts are not too small to be easily assembled by users or the assembly area is not too insufficient to lead to the components being easily loosened. The length and thickness range of the elbow assembly 3 ensure the overall size of the component won't be too large to add weight and press on the face, affecting the user's comfort. The diameter size ensures the overall ventilation effect of the patient interface assembly 1. When the elbow 31 is connected to the patient interface pad 2, the first interface end 311 of the elbow 31 deforms, ensuring that the elbow 31 can smoothly connect to the front interface end 21 of the patient interface pad 2. Furthermore, as shown in FIG. 9 and FIG. 18. The elbow assembly 3 includes at least one baffle 34. The baffle 34 can be continuous or discontinuous, and can have any contour shape, such as circular, triangular, square, etc. After the elbow assembly 3 is connected to the patient interface pad 2, it can limit the forward and backward movement of the frame 4. The outer diameter of the baffle 34 is approximately at or between 12 to 52 mm, the thickness is at or between 0.5 to 5 mm, and its material is consistent with the rigid part of the elbow assembly 3. When not subjected to external forces, the connection force between the patient interface pad 2 and the elbow assembly 3 is greater than the force required to separate them. When users detach the elbow assembly 3 from the patient interface pad 2, a force of at least 35N is required, ensuring that the patient interface assembly 1 does not easily fall off during normal use.

The frame 4 includes a positioning section 42, a through-opening 41, and support plates 43 extending in all directions. The positioning section 42 is configured to have a contour shape similar to the positioning component 25 on the patient interface pad 2, or to have magnetic attraction capabilities. The positioning section 42 can be positioned on the outer surface of the patient interface pad 2, limiting the rotation of the frame 4 relative to the patient interface pad 2. The diameter of the through-opening 41 of the frame 4 is approximately at or between 10 to 50 mm. It is configured to accommodate the front interface end 21 of the patient interface pad 2, or the elbow assembly 3, ensuring that the elbow assembly 3 can pass through, but not larger than the baffle 34 on the elbow assembly 3, to prevent the frame 4 from falling off. Furthermore, as shown in 12, the support plate 43 is an arbitrary contour extending from the perimeter of the through-opening 41 towards the facial side and can conform to the user's facial curve. It extends according to user's needs and preferences and serves the functions of connection, positioning, and stabilization. The frame 4 is at least partially rigid, and its material includes but is not limited to polyethylene, polypropylene, polycarbonate, polyester, silicone, thermoplastic elastomers, and the like, in one or more of material. In another embodiment, the elbow assembly 3 is used in conjunction with a nasal mask. In this embodiment, the elbow assembly 3 includes a connector 32 with a first end portion 321 and a second end portion 322. It also includes an elbow 31 with a first interface end 311, a second interface end 312, and an annular channel 313 that has a shaft bending (a shaft bending refers to a continuous force along the radial direction causing the shaft to bend, where "radial" refers to the direction along a diameter or radius, or perpendicular to the shaft direction). The elbow assembly also includes a baffle 34.

The patient interface assembly 1 includes an exhaust port 5, which allows the exhaled waste gas to flow from the inside of the assembly to the external environment. The exhaust port 5 can be set on the patient interface pad 2 or on the elbow assembly 3. The form of the exhaust port 5 can be hole-shaped or mesh-shaped. 1. When the exhaust port 5 is hole-shaped, the outer diameter of the exhaust hole is larger than the inner diameter (in another embodiment, the outer diameter of the exhaust port is smaller than the inner diameter of the exhaust port), and the ratio of their diameters does not exceed 2.45. The surface area of the exhaust hole on the outer surface of the patient interface pad 2 or the elbow assembly 3 is at or between 5 to 50%. At this time, the materials for the exhaust hole include but are not limited to polyethylene, polypropylene, polycarbonate, polyester, silicone, thermoplastic elastomer, etc. 2. When the exhaust port 5 is mesh-shaped, it can be in the form of a mesh formed from natural fabric or mesh-shaped knitted through a process (hand knitting or machine knitting). The surface area of the exhaust mesh on the outer surface of the patient interface pad 2 or the elbow assembly 3 is about at or between 5 to 80%. At this time, the materials for the exhaust mesh include but are not limited to polyethylene, polypropylene, polyester, nylon, natural fabrics, etc. 3. When the exhaust port is hole-shaped, it can also be used in conjunction with an external connector 7. The external connector 7 includes an external connection snap-fitting and noise reduction material. The noise reduction materials include but are not limited to polyethylene, polypropylene, cotton, nylon, natural fabrics, etc.

Figures 10A, 10B, 10C:
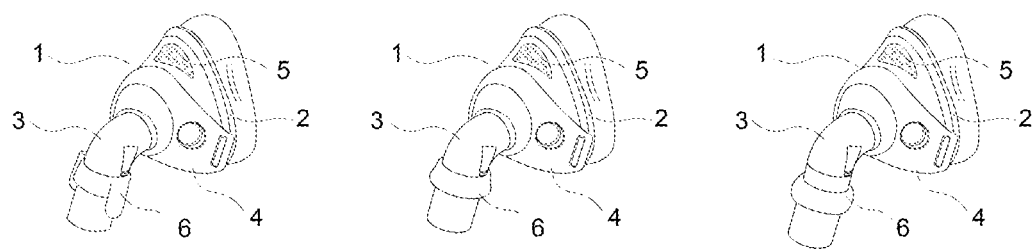
FIG. 10A, FIG. 10B, and FIG. 10C show schematic diagrams of the fixed form of a quick-release connector in accordance with an embodiment.
Figure 11A:
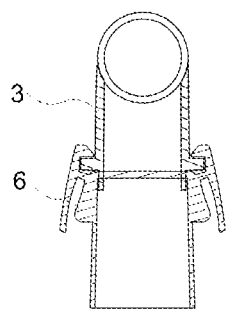
FIG. 11A, FIG. 11B, and FIG. 11C show sectional views of the fixed form of a quick-release connector in FIG. 10.
Figure 11B:
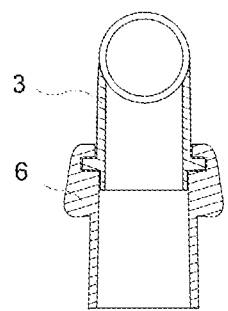
Figure 11C:
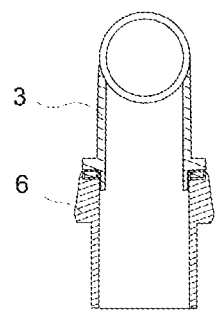
Figure 12A:
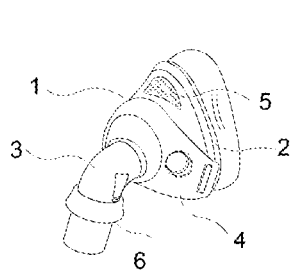
FIG. 12A, FIG. 12B, and FIG. 12C show schematic diagrams of a patient interface assembly matching different types of frames in accordance with an embodiment.
Figure 12B:
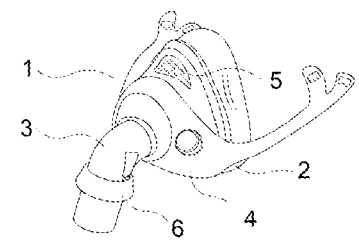
Figure 12C:
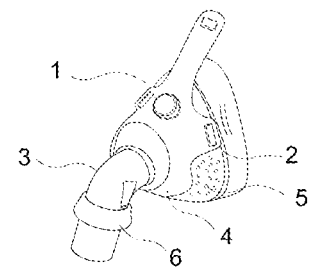

The quick-release connector 6 has an upper end, a lower end, and a fixing component. The upper end is configured to connect with the elbow assembly 3, and it can achieve rotation between the quick-release connector 6 and the elbow assembly 3. The lower end is configured to connect with the air supply tube. The upper end has a fixing component, which is used for faster release of the quick-release connector 6 and securing it to the elbow assembly 3. Furthermore, as shown in FIGS. 10 and 11. The fixing component includes but is not limited to clamps, snap-fits, and magnets. The external diameter of the upper end of the quick-release connector 6 is approximately at or between 10 to 50 mm, the external diameter of the lower end is approximately at or between 15 to 27 mm, the overall height is approximately at or between 10 to 45 mm, and the wall thickness is at or between 0.5 to 5 mm. This ensures that it can connect with the second end portion 322 of the elbow 31 and is compatible with air supply tubes with inner diameters of 15 mm or 22 mm. The material of the quick-release connector 6 can be polyethylene, polypropylene, polycarbonate, silicone, thermoplastic elastomers, etc. It should be noted that in this embodiment, the reason for directly connecting the elbow assembly 3 with the patient interface pad 2 is because there are many components in the mask system and the sealability between the components needs to be considered. In the process of assembling the mask system on their own, only when they operate carefully and install one-to-one, they can ensure the overall airtightness of the mask system. This disclosure connects the elbow assembly 3 directly to the patient interface pad 2, eliminating the intermediate step of connecting the frame 4. By reducing the number of connection points, the possibility of air leakage in the patient interface assembly 1 is reduced. Moreover, the frame 4 only needs to be simply positioned through the positioning component 25 and the positioning section 42, without aligning them one by one. This ensures the overall air-tightness of the patient interface assembly 1. Additionally, the forces between the components are reduced, making their connections more stable and the assembly process more convenient. Furthermore, the patient interface pad 2 can be either a nasal mask or a full face mask, providing patients with a variety of choices.

Designing the main body of frame 4 to have only one through-opening 41 is to allow the extension part of the frame 4 to take various contour forms, adapting to the needs of different patients, and the design between frame 4 and patient interface pad 2 is connected through positioning component 25, making the user interface more straightforward and understandable. The frame 4 only needs to ensure that the through-opening 41 can accommodate the front interface end 21 of the patient interface pad 2 and either the first interface end 311 of the elbow 31 in the elbow assembly 3 or the first end portion 321 of the connector 32. Components of the complex and cumbersome frame 4 mostly have a one-to-one correspondence, which means they need to be paired with a matching set to be used. Patients cannot choose their preferred type of frame 4 for long-term treatment as much as possible, and corresponding connections are also required to ensure the overall system's air-tightness. The simplified frame 4 components no longer need to be paired with a corresponding system. Patients can freely choose their preferred frame 4 and can replace the frame 4 separately based on their needs. Moreover, the simplified frame 4 can extend the lifespan of the components. The frame 4 and other components don't need to endure multiple disassemblies and wear, making them simpler in both cleaning and manufacturing.

The following illustrates several structures of patient interface assembly in this disclosure based on specific embodiments:

Embodiment 1

Figure 5A:
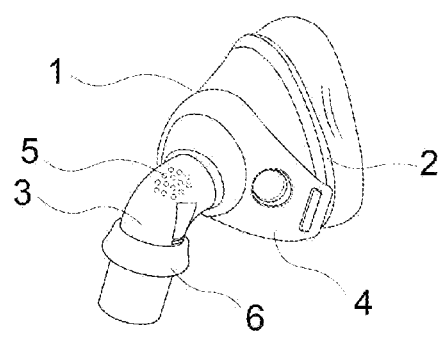
FIG. 5A and FIG. 5B show schematic diagrams of an exhaust port set on an elbow assembly in accordance with Embodiment 1.
Figure 5B:
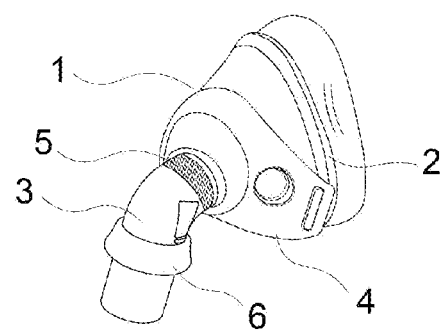
Figure 6A:
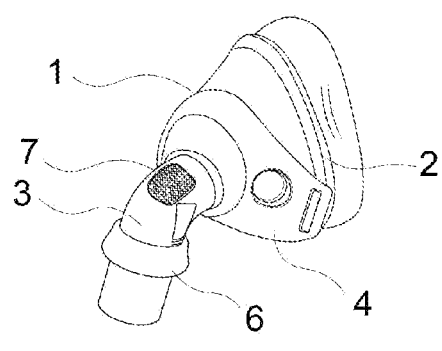
FIG. 6A and FIG. 6B show schematic diagrams of an exhaust port set on an patient interface pad in accordance with Embodiment 1.
Figure 6B:
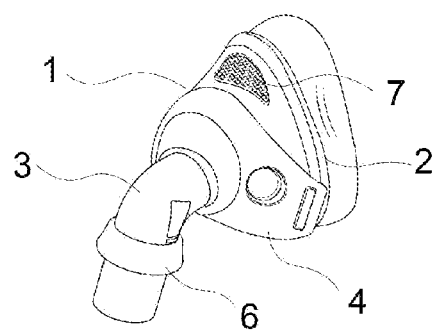

A patient interface assembly 1 in the embodiment is configured to longitudinally contact an area between a nose bridge and chin and form a seal to the oral and nasal airways, or longitudinally contact the area between the nose bridge and upper lip and form a seal to a nasal airway, and the patient interface assembly 1 is also configured to communicate equipment with the airways to transmit positive pressure air or breathable gas for medical treatment. The patient interface assembly includes: a patient interface pad 2, a frame 4, an elbow assembly 3, and a quick-release connector 6. The patient interface pad 2 has a front interface end 21 that connects with the elbow assembly 3 and a rear interface end that seals at least one airway of the patient. The elbow assembly 3 is directly connected to the front interface end 21 of the patient interface pad 2 and can rotate relative to it. The quick-release connector 6 is connected to the elbow assembly 3, and they can rotate relative to each other. An exhaust port 5 is set on the patient interface assembly 1, allowing the exhaled waste gas to flow from the inside of the assembly to the external environment. As shown in FIGS. 5 and 6, the exhaust port 5 can be set on the patient interface pad 2 or on the elbow assembly 3. The exhaust port 5 is a through hole. The forms can be smaller diameter holes being arranged to form a piece or a ring of exhaust holes that has a contour shape, or can be a larger diameter hole connected to an exhaust net with noise reduction capabilities. When the exhaust port 5 is a series or circle of holes, the outer diameter of the hole is larger than the inner diameter (in another embodiment, the outer diameter of the exhaust port is smaller than the inner diameter), which can reduce the noise of airflow jetting, allowing the airflow to quickly pass through the small holes, avoiding blockage that can cause turbulent vortex formation and thus generate noise. When the exhaust port 5 is connected to a noise reduction net, the noise reduction net is a mesh-like structure that can be formed from natural fabric or mesh-shaped knitted through a process. Due to the material and structure of the noise reduction net, when the airflow passes through the exhaust port 5, it can be dispersed by the noise reduction net on the exhaust port 5 and flow outwards, achieving the purpose of reducing noise. Specifically, as shown in FIG. 5, the exhaust port 5 is located on the elbow assembly 3. The optimal placement for the exhaust port 5 is on the first end portion 321 of the connector 32 in the elbow assembly 3 or the area the first interface end 311 of the elbow 31 projected onto the annular channel 313. This arrangement allows the exhaled waste gas to flow in line from the inside of the elbow assembly 3 to the external environment, preventing the exhaled waste from clashing with the positive pressure air supplied by the respirator. This maintains an unobstructed airway. Furthermore, placing the exhaust port 5 on the elbow assembly 3 keeps it far from the ears. By controlling the distance, the overall noise of the patient interface assembly 1 can be controlled and reduced, making it more friendly for patients who have a high requirement for sleeping environment. Further, as shown in FIG. 6, the exhaust port 5 is located on the patient interface pad 2, which is closer to the mouth and nasal airway. This placement effectively discharges the carbon dioxide and waste gas exhaled by the patient, preventing the re-inhalation of the exhausted gases. Additionally, when the gas passes through the exhaust port 5 set on the patient interface pad 2, the outgoing airflow slightly lifts the patient interface pad 2 upwards. This can reduce the pressure of the patient interface pad 2 on the face, thereby diminishing the feeling of foreign objects when the patient uses the patient interface assembly 1.

Figure 7A:
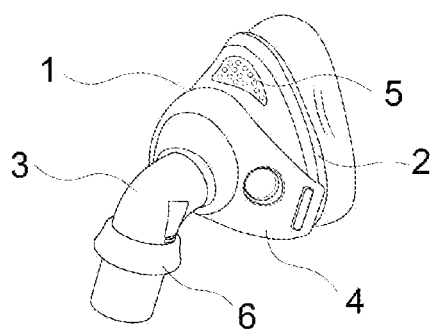
FIG. 7A and FIG. 7B show schematic diagrams of an exhaust port with an external connector in accordance with Embodiment 1.
Figure 7B:
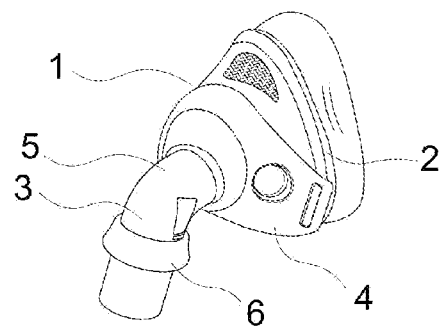
Figure 8A:
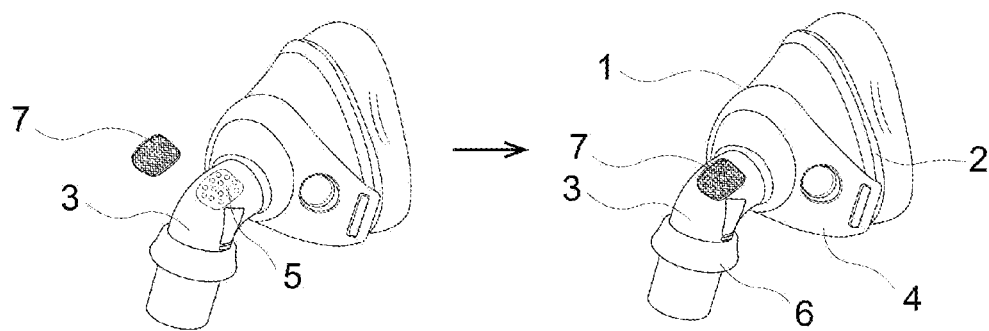
FIG. 8A and FIG. 8B show schematic diagrams of an exhaust port used in conjunction with an external connector in accordance with Embodiment 1.
Figure 8B:
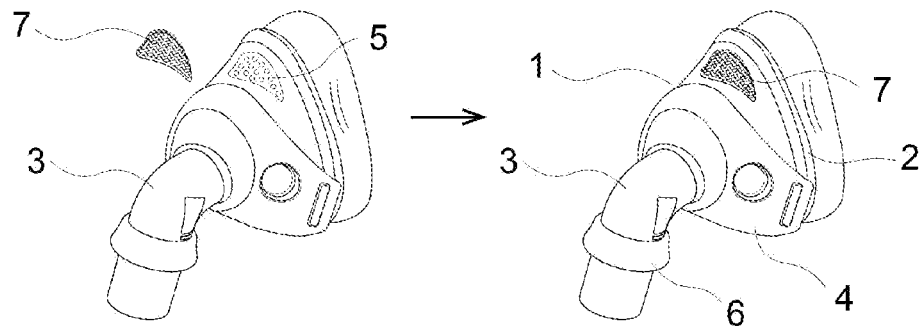

In another embodiment, as shown in FIGS. 7 and 8, the exhaust port 5 can be used in conjunction with an external connector 7, which includes an external connection snap-fitting and noise reduction material. The external connection snap-fitting can be externally attached to the surface of the exhaust port 5. The outer edge of the external connection clip is larger than the outer contour of the exhaust port 5, allowing the exhaust port 5 to be wrapped within the external connector 7. The noise reduction material can be directly placed between the external connection snap-fitting and the exhaust port 5, or it can be connected to the external connection snap-fitting. The connection methods can be heat pressing, adhesive bonding, and other methods. The form of the noise reduction material can be natural fabric or industrially woven mesh, and that the noise reduction material has enough gaps to release waste gas is ensured, therefore dispersing airflow through these gaps to achieve the purpose of noise reduction. The noise reduction material can be made from polyester fiber, fiberglass, polyethylene, polyurethane, rubber, or other porous materials. Patients can choose whether or not to wear the external connector 7 based on their preferences: For patients with a high exhalation flow; they can choose the patient interface assembly 1 with just noise reduction holes, which can help discharge waste more quickly. For patients with a normal or smaller exhalation flow, they can choose the patient interface assembly 1 with the external connector 7, which can help create a more comfortable and quiet sleeping environment for the patient.

Embodiment 2

A patient interface assembly 1 is configured to longitudinally contact an area between a nose bridge and chin and form a seal to the oral and nasal airways, or longitudinally contact the area between the nose bridge and upper lip and form a seal to the nasal airway, and the patient interface assembly 1 is also configured to communicate equipment with the airways to transmit positive pressure air or breathable gas for medical treatment. The patient interface assembly includes: the patient interface pad 2, frame 4, elbow assembly 3, and quick-release connector 6. The patient interface pad 2 has a front interface end 21 that connects to the first interface end 311 of the elbow 31 in the elbow assembly 3 and a rear interface end that seals at least one airway of the patient. The elbow assembly 3 includes an elbow 31. The elbow 31 has a first interface end 311 that directly connects with the front interface end 21 of the patient interface pad 2, and relative rotation between elbow 31 and patient interface assembly is allowed. The elbow 31 also has a second interface end 312 that connects with the quick-release connector 6, allowing the elbow 31 and quick-release connector 6 to rotate relative to each other. The patient interface assembly 1 includes an exhaust port 5, allowing the exhaled waste gas to flow from the inside of the patient interface assembly 1 to the external environment.

Figures 14A, 14B, 14C:
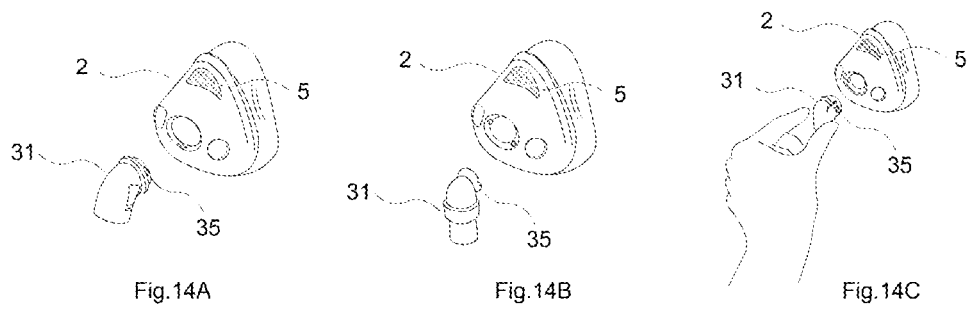
FIG. 14A, FIG. 14B, and FIG. 14C show schematic diagrams of different connection methods between an elbow assembly and a patient interface pad in accordance with Embodiment 2.

As shown in FIG. 14, the elbow assembly 3 can be connected to the patient interface pad 2 in various ways to achieve the purpose of allowing the elbow assembly 3 to rotate relative to the patient interface pad 2 within at least one plane. Specifically, as shown in FIG. 14A, the elbow assembly 3 only includes the elbow 31 that connects to the patient interface pad 2. The connection method between the elbow assembly 3 and the patient interface pad 2 can be a snap-fitting, a snap buckle, etc., allowing the elbow assembly 3 to rotate 360° within the plane parallel to the front interface end 21 of the patient interface pad 2. The exhaust port 5 can be set on the patient interface pad 2 or the elbow 31. As shown in FIG. 14B, the elbow assembly 3 only includes the elbow 31 that connects to the patient interface pad 2. The connection method between the elbow assembly 3 and the patient interface pad 2 can be a hinge, a ball socket, a snap-fitting, in one of the above methods or more. This design allows the elbow assembly 3 to rotate within the plane perpendicular to the coronal plane of the patient interface pad 2. The exhaust port 5 can be set on the patient interface pad 2 or the elbow 31. As shown in FIG. 14C, the elbow assembly 3 only includes the elbow 31 that connects to the patient interface pad 2. The deformable material of the elbow 31 can be silicone, thermoplastic elastomer, and the like. Due to the deformable material properties of the elbow 31, it can achieve connection with the patient interface pad 2 through its own deformation. This reduces the possibility of wear on the elbow 31 caused by patients frequently plugging and unplugging it. Moreover, the deformable material can reinforce the sealing of connection gaps, thereby enhancing the overall air tightness of the component.

Embodiment 3

A patient interface assembly 1 in the embodiment is configured to longitudinally contact an area between a nose bridge and chin and form a seal to the oral and nasal airways, or longitudinally contact the area between the nose bridge and upper lip and form a seal to the nasal airway, and the patient interface assembly 1 is also configured to communicate equipment with the airways to transmit positive pressure air or breathable gas for medical treatment. The patient interface assembly includes: a patient interface pad 2, a frame 4, an elbow assembly 3, and a quick-release connector 6. The patient interface pad 2 has a front interface end 21 that connects to the first interface end 311 of the elbow 31 in the elbow assembly and a rear interface end that seals at least one airway of the patient.

The elbow assembly 3 includes a connector 32 and an elbow 31. The connector 32 has a first end portion 321 that directly connects to the front interface end 21 of the patient interface pad 2. The connector 32 can rotate relative to the patient interface pad 2. The connector 32 also has a second end portion 322 connected to the first interface end 311 of the elbow 31, and the connector 32 can rotate relative to the elbow 31. The elbow 31 is provided with a first interface end 311 that directly connects to the second end portion 322 of the connector 32, and the elbow 31 is capable of rotation relative to the connector 32. The elbow 31 also has a second interface end 312 that connects to the quick-release connector 6, and the elbow 31 can rotate relative to the quick-release connector 6. The patient interface assembly 1 includes an exhaust port 5, allowing the exhaled waste gas to flow from the inside of the patient interface assembly 1 to the external environment.

Figure 15A:
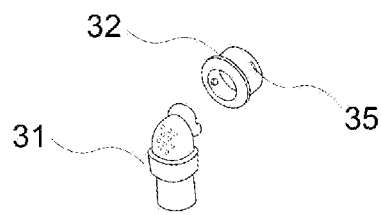
FIG. 15A, FIG. 15B, FIG. 15C and FIG. 15D show schematic diagrams of different connection methods between a connector and an elbow in elbow assembly in accordance with Embodiment 3.
Figure 15B:
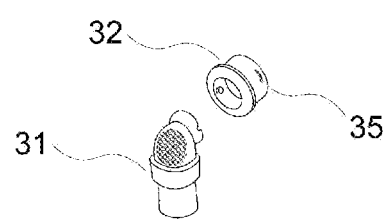
Figure 15C:
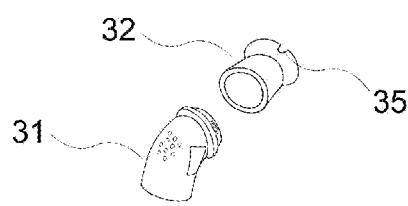
Figure 15D:
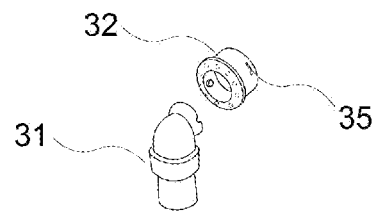

As shown in FIG. 15A, the elbow assembly 3 contains a connector 32 that connects to the patient interface pad 2, as well as an elbow 31 connected to the connector 32. The connection between the connector 32 and the patient interface pad 2 can be achieved through mechanisms such as a snap-fitting or a snap buckle, allowing the connector 32 to rotate 360° within a plane parallel to the front interface end 21 of the patient interface pad 2. The connection between the elbow 31 and the connector 32 can be a hinge, a ball and socket joint, a snap-fitting, or a combination thereof, enabling the elbow 31 to rotate relative to the connector 32 within a plane perpendicular to the coronal plane of the patient interface pad 2. The elbow assembly 3 is thus capable of rotating 360° relative to the patient interface pad 2 within a plane parallel to the front interface end 21 of the patient interface pad 2 and can also rotate in a plane perpendicular to the coronal plane of the patient interface pad 2 relative to the patient interface pad 2. As shown in FIG. 15A, the exhaust port 5 can be located on the elbow 31. As shown in FIG. 15B, the exhaust port 5 can be used in conjunction with an external connector 7. As shown in FIG. 15D, the exhaust port 5 can be positioned on the connector 32. As shown in FIG. 15C, the elbow assembly 3 includes a connector 32 that attaches to the patient interface pad 2 and an elbow 31 connected to the connector 32. The connection between the connector 32 and the patient interface pad 2 can be a ball socket, hinge, or a combination thereof, to make the elbow 31 rotate relative to connector 32 within a plane perpendicular to the coronal plane of the patient interface pad 2. The elbow assembly 3 can rotate 360° relative to the patient interface pad 2 in a plane parallel to the front interface end 21 of the patient interface pad 2, and the elbow assembly can also rotate relative to the patient interface pad 2 in a plane perpendicular to the coronal plane of the patient interface pad 2. The exhaust port 5 is positioned on the elbow assembly 3 but can also be set up on the patient interface pad 2.

Embodiment 4

A patient interface assembly in the embodiment is configured to longitudinally contact an area between a nose bridge and chin and form a seal to the oral and nasal airways, or longitudinally contact the area between the nose bridge and upper lip and form a seal to the nasal airway. The patient interface assembly 1 is also configured to communicate equipment with the airways to transmit positive pressure air or breathable gas for medical treatment. The patient interface assembly includes: a patient interface pad 2, a frame 4, an elbow assembly 3, and a quick-release connector 6. The patient interface pad 2 has a front interface end 21 that connects with the elbow assembly and a rear interface end that seals at least one airway of the patient. The elbow assembly 3 is directly connected to the front interface end 21 of the patient interface pad 2 and can rotate relative to it. The quick-release connector 6 is connected to the elbow assembly 3, and they can rotate relative to each other. The patient interface assembly 1 includes an exhaust port 5, which allows the exhaled waste gas to flow from the inside of the patient interface assembly 1 to the external environment.

Figure 16A:
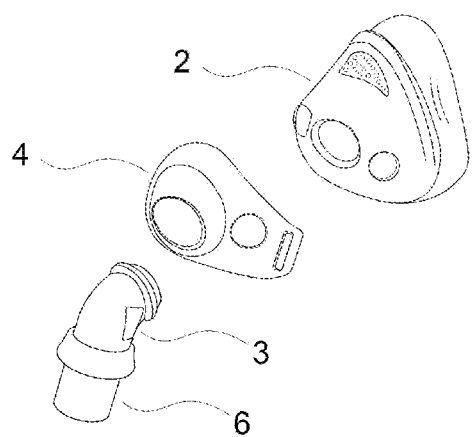
FIG. 16A and FIG. 16B show schematic diagrams of the detachable or non-detachable connection between an elbow assembly and a frame in accordance with Embodiment 4.
Figure 16B:
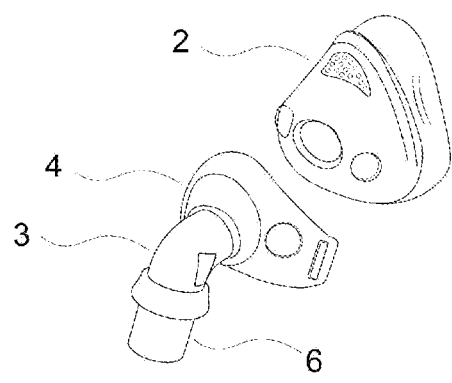

As shown in FIG. 16, the frame 4 and the elbow assembly 3 can be in two forms: 1. They can be detachable: 2. They are non-detachable. The patient interface assembly 1 has the elbow assembly 3 and frame 4 in a detachable form, which can conveniently allow the patient to easily disassemble and clean and maintain the assembly, avoid hidden corners that harbor dirt and bacteria, and help keep the assembly hygienic. the patient interface assembly 1 is designed with the elbow assembly 3 and the frame 4 in a non-detachable form, making it easier for the patient to assemble and ensuring a more stable structure. The secure contact between the frame 4 and the elbow assembly 3 ensures that the product does not move or loosen during use, thereby guaranteeing a reliable user experience with the whole component.

Implementing the patient interface assembly in the disclosure provides at least the following beneficial effects:
1. Reducing the connection steps between components results in fewer failure points, reducing the overall product's malfunction rate and therefore enhancing the overall component's air-tightness. In the market, most mask systems or nasal systems are assembled through the connection method of patient interface pad-frame-elbow. This common approach includes two uncontrollable leakage risks, which are between the patient interface pad and the frame, and between the frame and the elbow: but complex and lengthy installation steps can increase the risk of operational errors, leading to incorrect or incomplete assembly. This can subsequently impact the product's performance and reliability, resulting in issues like poor sealing, improper fitting, and wear and tear. When patients are unfamiliar with the assembly process of the components, there's a high likelihood of situation of air leaks after assembly. Given that there are at least 4 to 5 fundamental connections within the entire treatment system, it makes it more challenging for patients to identify the reason of the leak. After prolonged use by the patient, since the patient interface assembly needs to be frequently disassembled and cleaned, the sealing at the connection area is highly susceptible to external damage, leading to reduced air-tightness. Directly connecting the patient interface pad to the elbow assembly and eliminating the step of connecting the patient interface pad to the frame has following advantages: a. When the gas is in the patient interface assembly, it only needs to pass directly through one tube, with fewer gaps when flowing through the tube, reducing the risk of leakage in the whole assembly: b. The assembly process is simplified. When patients assemble the components, they don't need to install them one by one. They only need to position the frame on the surface of the patient interface pad, and connect the elbow assembly to the patient interface pad. The patient interface pad and the elbow assembly automatically form a position to accommodate the frame, and can limit the relative movement between the frame and the two, making it easier for patients to assemble the new product. c. The installation steps are redesigned, reducing the connection points from two to one, letting the overall structure that is constructed by all the respiratory components simplified, reducing the chances of errors during the installation process and decreasing the occurrence of poor or incorrect assembly. By designing a user-friendly installation interface and providing clear guidance, and by using the assembly process that is easy to operate, it allows users to complete product assembly more effortlessly and reducing potential points of failure during installation, thereby lowering the failure rate during the product's operation.

2. Modular combination, more choices. Because the installation step of the frame is eliminated, the importance of the frame in the installation steps is diminished. The frame is limitingly positioned to some extent by the groove formed by the connection of the baffle of the elbow assembly with the patient interface pad. Therefore, the basic part of the frame only needs to include the sidewall that can accommodate part of the mask, the through-opening that allows the elbow assemblies to pass through and matches with the patient interface pad, and the positioning section on the frame that can be matched with the mask positioning component. Apart from the basic parts, the frame can have more choices on its shape design, which can provide corresponding frames for patients who have different needs or preferences. There's no longer a need to design frames with different connection methods for different elbow and patient interface pad. It's not necessary to consider the impact of frame on the overall air-tightness of the whole assembly, and the focus can solely be on the comfort of the patient when wearing it. In production, the basic connection structure between the patient interface pad and the elbow assembly is also simplified, while important functional structures such as exhaust holes and anti-asphyxiation valves do not need to be changed. The reduction in the processing steps for the overall connection structure means that, with the connection between the elbow assemblies and the patient interface pad being fixed, it's only necessary to modularly develop a structurely simple frame. This greatly reduces the processing complexity and R&D costs of the patient interface assembly 1, while offering a variety of frame combinations to meet various user's needs.

3. The connection between the components is more stable. Compared to the connection of the patient interface pad-frame-elbow; the connection method of the patient interface pad-elbow assembly is more stable. The direct connection design of the elbow assemblies and the patient interface pad, based on the original connection method, adds radial support from the elbow assembly to the frame and limits and secures the frame through the baffle of the elbow assembly. The connection points have also been simplified from two to one, making it less likely to come loose. Without the application of external force, in the connection method of the patient interface pad-frame-elbow; the patient interface pad is subjected to the gravitational pull of the frame and the elbow: while, in the connection method of the patient interface pad-elbow assembly, the patient interface pad is only subjected to the gravitational pull of the elbow assembly. Comparing the two, the assembly method of the former increases the risk of the patient interface assembly falling off under the influence of tension. In contrast, the assembly design of the latter reduces the risk of component detachment, making it more stable and less prone to falling off.

4. Compared to other products with quick-release elbows, the patient interface assembly has fewer components and is lighter in overall weight. Most existing products connect the elbow assembly, which has a clip structure on both sides, directly to the frame, and the lower end of the elbow is detachably connected to the air supply hose. At this time, due to the presence of the quick-release connection structure on the elbow assembly, it adds weight to the patient interface system. Therefore, by separating the quick-release system on the elbow assembly and designing the elbow assembly to be directly detachable with the patient interface pad, the overall weight of the patient interface assembly is reduced. Meanwhile, quick-release parts can be selected based on the personal wearing preferences. When the patient interface assembly is directly connected through the elbow; the overall parts of the component are more lightweight and easier to use compared to the existing mask systems. By simplifying the structure of the elbow to reduce its weight and reducing the number of parts on the elbow; the overall number of components is reduced.

5. The simplification of individual component structures can reduce costs, and they are also easier to clean and more environmentally friendly: a. The design of the frame 4 eliminates the snap-fitting connection structure, making the model structure simpler. This can reduce the processing steps and complexity, thereby lowering the costs during the processing and manufacturing process. Changes in corresponding mold making and corresponding mold-opening methods reduce the investment and maintenance costs of equipment and molds: simple component structures make it easier to conduct quality inspection and control, reducing the occurrence of defective products and lowering inspection costs. The simplified structure leads to a smaller volume and lighter weight, making stacking and placing components easier, thus reducing transportation costs. When the frame component is damaged, only a new frame needs to be replaced, and there are more choices available. There's no need to consider the connection issues between components, providing patients with a more comfortable experience. The assembly of modular components, for production, can extend the lifespan of each component, helping reduce energy consumption and waste material during the manufacturing process. By reducing energy consumption and waste material and recycling some components, carbon emissions in production are decreased, and the environment is protected. b. With the simplified design of frame and the corresponding adjustments of the patient interface pad and elbow assembly, it makes the product easier to use, there are fewer connections and fixtures in the components. As a result, they are easier to disassemble and clean when needed. The simple structure reduces the presence of hygiene blind spots and a concave-convex surface, minimizing the chances of impurities and dirt accumulation, making the cleaning process easier and more thorough. Complex components might require more detergents and tools for thorough cleaning, while simpler components achieve the same cleanliness with fewer quantities, reducing the use of chemical cleaning agents. This saves energy and time and is environmentally beneficial.

The above descriptions of the disclosure's embodiments are illustrated with reference to the accompanying drawings, but the disclosure is not limited to these specific embodiments. The described embodiments are merely illustrative and not restrictive. Those skilled in the art can make different modifications and variations under the guidance of this disclosure, without departing from the scope and spirit protected by the claims of this disclosure. All such modifications and variations are within the scope of the disclosure's protection.

It must be noted that as used herein and in the appended claims, the singular forms "a", "an", and "the" include their plural equivalents, unless the context clearly dictates otherwise.

The invention claimed is:

1. A patient interface assembly configured to longitudinally contact an area between a nose bridge and a chin to form a seal to an oral airway and a nasal airway, or to longitudinally contact an area between the nose bridge and an upper lip to form a seal to the nasal airway, wherein the patient interface assembly is also configured to communicate equipment with the airways to transmit positive pressure air or breathable gas for medical treatment, the patient interface assembly comprising:
 a patient interface pad comprising a front interface end, a rear interface end, a support element that at least partially contacts a side wall of a frame, a sealing element with a cushioning structure, and a positioning component that contacts the frame,
 wherein the front interface end of the patient interface pad is configured to rotatably and directly connect to a first interface end of an elbow assembly,
 wherein the rear interface end is configured to seal at least one of the airways;
 wherein the elbow assembly includes an elbow with the first interface end, a second interface end, and a shaft bending annular channel,
 wherein the elbow includes a fixed structure configured to be connectable to the front interface end of the patient interface pad, the second interface end being configured to be rotatably connectable to a quick-release connector, and wherein a baffle extends outwardly from an outer surface of the elbow assembly to limit forward and backward movement of the frame;
 wherein the frame includes a positioning section, at least one through-opening, and a support plate extending around from the through-opening,
 wherein the positioning section is configured to position the frame onto the patient interface pad;
 wherein an exhaust port is provided on the elbow assembly to allow exhaled waste gas to flow from an inside of the patient interface pad to an external environment;
 wherein the quick-release connector includes an upper end, a lower end, and a fixing component, and the upper end is configured to directly and detachably connect to the second interface end of the elbow assembly; and
 wherein the positioning component has a contour shape to match the positioning section on the frame and is configured to limit a relative rotation between the frame and the patient interface pad.

2. The patient interface assembly according to claim 1, wherein the support plate on the frame extends from a perimeter of the through-opening towards a side facing a face to form any contour.

3. The patient interface assembly according to claim 1, wherein the exhaust port has a form of a through-hole or a mesh-like structure, and when the exhaust port is the mesh-like structure, a material of the exhaust port includes a noise reduction material.

4. The patient interface assembly according to claim 1, wherein the fixing component of the quick-release connector is provided at the upper end of the quick-release connector, and a form of the fixing component includes a clip, a snap-fitting, or a magnet.

5. The patient interface assembly according to claim 1, wherein a connection method between the support element of the patient interface pad and the sealing element includes one or more of a molding, an adhesive bonding, or a mechanical connection.

6. The patient interface assembly according to claim 1, wherein the fixed structure on the elbow assembly is one or more of a hinge, a ball socket, a snap-fitting, or a magnet.

7. A patient interface assembly configured to longitudinally contact an area between a nose bridge and a chin to form a seal to an oral airway and a nasal airway, or to longitudinally contact an area between the nose bridge and an upper lip to form a seal to the nasal airway, wherein the patient interface assembly is also configured to communicate equipment with the airways to transmit positive pressure air or breathable gas for medical treatment, the patient interface assembly comprising:
 a patient interface pad comprising a front interface end, a rear interface end, a support element that at least partially contacts a side wall of a frame, a sealing element with a cushioning structure, and a positioning component that contacts the frame,
 wherein the front interface end of the patient interface pad is configured to rotatably and directly connect to a first interface end of an elbow assembly,
 wherein the rear interface end is configured to seal at least one of the airways;
 wherein the elbow assembly includes an elbow with the first interface end, a second interface end, and a shaft bending annular channel,
 wherein the elbow assembly includes a fixed structure configured to be connectable to the front interface end of the patient interface pad, the second interface end being configured to be rotatably connectable to a quick-release connector, and wherein a baffle extends outwardly from an outer surface of the elbow assembly to limit forward and backward movement of the frame;
 wherein the frame includes a positioning section, at least one through-opening, and a support plate extending around from the through-opening,
 wherein the positioning section is configured to position the frame onto the patient interface pad;
 wherein an exhaust port is provided on the elbow assembly to allow exhaled waste gas to flow from an inside of the patient interface pad to an external environment, wherein the exhaust port has a form of a through-hole, a mesh-like structure, or gaps of a noise reduction material;

wherein the quick-release connector includes an upper end, a lower end, and a fixing component, and the upper end is configured to directly and detachably connect to the second interface end of the elbow assembly; and wherein the positioning component has a contour shape to match the positioning section on the frame and is configured to limit a relative rotation between the frame and the patient interface pad.

8. The patient interface assembly according to claim 7, wherein the noise reduction material includes polyethylene, polypropylene, cotton, nylon and natural fabrics.

9. The patient interface assembly according to claim 7, wherein the baffle is discontinuous.

10. The patient interface assembly according to claim 7, wherein the fixing component of the quick-release connector is provided at the upper end of the quick-release connector, and a form of the fixing component includes a clip, a snap-fitting, or a magnet.

11. A patient interface assembly configured to longitudinally contact an area between a nose bridge and a chin to form a seal to an oral airway and a nasal airway, or to longitudinally contact an area between the nose bridge and an upper lip to form a seal to the nasal airway, wherein the patient interface assembly is also configured to communicate equipment with the airways to transmit positive pressure air or breathable gas for medical treatment, the patient interface assembly comprising:

a patient interface pad comprising a front interface end, a rear interface end, a support element that at least partially contacts a side wall of a frame, a sealing element with a cushioning structure, and a positioning component that contacts the frame, wherein the front interface end of the patient interface pad is configured to rotatably and directly connect to a first interface end of an elbow assembly, wherein the rear interface end is configured to seal at least one of the airways;

wherein the elbow assembly includes an elbow with the first interface end, a second interface end, and a shaft bending annular channel, wherein the elbow includes a fixed structure configured to be connectable to the front interface end of the patient interface pad, the second interface end being configured to be rotatably connectable to a quick-release connector, and wherein a baffle extends outwardly from an outer surface of the elbow assembly to limit forward and backward movement of the frame, wherein the frame includes a positioning section, at least one through-opening, and a support plate extending around from the through-opening, wherein the positioning section is configured to position the frame onto the patient interface pad, wherein an exhaust port is provided on the elbow assembly to allow exhaled waste gas to flow from an inside of the patient interface pad to an external environment, wherein the quick-release connector includes an upper end, a lower end, and a fixing component, and the upper end is configured to connect to the second interface end of the elbow assembly, wherein an outer diameter of the upper end of the quick-release connector is between 10 mm to 50 mm, an outer diameter of the lower end is between 15 mm to 27 mm, and wherein the positioning component has a contour shape to match the positioning section on the frame and is configured to limit a relative rotation between the frame and the patient interface pad.

12. The patient interface assembly according to claim 11, wherein the lower end of the quick-release connector is connectable to an air supply tube with an inner diameter of 15 mm or 22 mm.

13. The patient interface assembly according to claim 11, wherein a form of the exhaust port is hole-shaped or mesh-shaped.

14. The patient interface assembly according to claim 11, wherein an overall height of the quick-release connector is between 10 mm to 45 mm.

15. A patient interface assembly configured to longitudinally contact an area between a nose bridge and a chin to form a seal to an oral airway and a nasal airway, or to longitudinally contact an area between the nose bridge and an upper lip to form a seal to the nasal airway, wherein the patient interface assembly is also configured to communicate equipment with the airways to transmit positive pressure air or breathable gas for medical treatment, the patient interface assembly comprising:

a patient interface pad comprising a front interface end, a rear interface end, a support element that at least partially contacts a side wall of a frame, a sealing element with a cushioning structure, and a positioning component that contacts the frame, wherein the front interface end of the patient interface pad is configured to rotatably and directly connect to a first interface end of an elbow assembly, wherein the rear interface end is configured to seal at least one of the airways, wherein the elbow assembly includes an elbow with the first interface end, a second interface end, and a shaft bending annular channel, wherein the elbow assembly includes a fixed structure configured to be connectable to the front interface end of the patient interface pad, the second interface end being configured to be rotatably connectable to a quick-release connector, and wherein a baffle extends outwardly from an outer surface of the elbow assembly to limit forward and backward movement of the frame, wherein the frame includes a positioning section, at least one through-opening, and a support plate extending around from the through-opening, wherein the positioning section is configured to position the frame onto the patient interface pad, wherein an exhaust port is provided on the elbow assembly to allow exhaled waste gas to flow from an inside of the patient interface pad to an external environment, wherein the quick-release connector includes an upper end, a lower end, and a fixing component, and the upper end is configured to directly and detachably connect to the second interface end of the elbow assembly, wherein an outer diameter of the baffle is between 12 mm to 52 mm, and wherein the positioning component has a contour shape to match the positioning section on the frame and is configured to limit a relative rotation between the frame and the patient interface pad.

16. The patient interface assembly according to claim 15, wherein a thickness of the baffle is between 0.5 mm to 5 mm.

17. The patient interface assembly according to claim 15, wherein the elbow assembly includes one or more of the following materials: polyethylene, polyamide, polypropylene, polycarbonate, polyester, silicone, or thermoplastic elastomer.

18. The patient interface assembly according to claim 15, wherein the fixing component of the quick-release connector is provided at the upper end of the quick-release connector, and a form of the fixing component includes a clip, a snap-fitting, or a magnet.

\* \* \* \* \*